US008653027B2

(12) United States Patent
Cohen et al.

(10) Patent No.: US 8,653,027 B2
(45) Date of Patent: Feb. 18, 2014

(54) METHOD OF TREATMENT OF TYPE-1 DIABETES WITH HUMANIN ANALOGUES

(75) Inventors: Pinchas Cohen, Pacific Palisades, CA (US); Kuk-Wha Lee, Oakland, CA (US)

(73) Assignee: The Regents of the University of California, Oakland, CA (US)

(*) Notice: Subject to any disclaimer, the term of this patent is extended or adjusted under 35 U.S.C. 154(b) by 20 days.

(21) Appl. No.: 13/180,181

(22) Filed: Jul. 11, 2011

(65) Prior Publication Data

US 2012/0021981 A1 Jan. 26, 2012

Related U.S. Application Data

(62) Division of application No. 12/210,856, filed on Sep. 15, 2008, now Pat. No. 7,998,928.

(60) Provisional application No. 60/972,596, filed on Sep. 14, 2007.

(51) Int. Cl.
*A61K 38/00* (2006.01)

(52) U.S. Cl.
USPC .................................. 514/6.9; 514/1.1

(58) Field of Classification Search
None
See application file for complete search history.

(56) References Cited

U.S. PATENT DOCUMENTS

| 7,452,867 B2 * | 11/2008 | Gozes et al. ............ 514/1.1 |
| 7,998,928 B2 | 8/2011 | Cohen et al. |
| 8,076,449 B2 * | 12/2011 | Chiba et al. ............ 530/300 |
| 2006/0246047 A1 | 11/2006 | Imoto et al. |
| 2008/0039393 A1 | 2/2008 | Mascarenhas |
| 2010/0130412 A1 | 5/2010 | Cohen et al. |

FOREIGN PATENT DOCUMENTS

| WO | PCT/JP2005/007286 | * 10/2005 | ........... A61K 38/00 |
| WO | WO 2008/153788 | 12/2008 | |

OTHER PUBLICATIONS

Arata, M. et al., "Effect of Modified Diabetic Splenocytes on Mice Injected with Splenocytes from Multiple Low-Dose Streptozotocin Diabetic Donors," *Exp. Biol. Med.*, 2001, vol. 226, No. 10, pp. 898-905.
Chiba, T. et al., "Development of a Femtomolar-Acting Humanin Derivative Named Colivelin by Attaching Activity-Dependent Neurotrophic Factor to Its N Terminus: Characterization of Coliveline-Mediated Neuroprotection against Alzheimer's Disease-Relevant Insults In Vitro and In Vivo," *The Journal of Neuroscience*, Nov. 2, 2005, vol. 25, No. 44, pp. 10252-10261.
Cobb, L. et al., "Site-Specific Phosphorylation by Intracellular Kinases Determines the Apoptotic Activity of IGFBP-3," *Growth Hormone & IGF Research*, Abstracts, 3 In!. Congress of GRS & IGF Society, 2006, Abstract No. OR04-6, p. S8.
Cobb, L.J. et al., "Phosphorylation of Ser-156 by DNA-PK Is Functionally Critical for Apoptosis Induction by IGFBP-3," *The Endocrine Society Program & Abstracts, 8d Annual Meeting*, Jun. 24-27, 2006, Boston, MA, Abstract No. P1-201, 2 pages.

Eisenbarth, G.S., "Update, Update in Type 1 Diabetes," *The Journal of Clinical Endocrinology & Metabolism*, 2007, vol. 92, No. 7, pp. 2403-2407.
Eizirik, D.L. et al., "A choice of death—the signal-tramsduction of immune-mediated betacell apoptosis," *Diabetologica*, 2001, vol. 44, pp. 2115-2133.
Guo, B. et al., "Bcl-G, a Novel Pro-apoptotic Member of the Bcl-2 Family," *The Journal of Biological Chemistry*, Jan. 26, 2001, vol. 276, No. 4, pp. 2780-2785.
Guo, B. et al., "Humanin peptide suppresses apoptosis by interfacing with Bax activation," *Nature*, May 23, 2003, vol. 423, pp. 456-461.
Hashimoto, Y. et al., "A rescue factor abolishing neuronal cell death by a wide spectrum of familial Alzheimer's disease genes and A13," *PNAS*, May 22, 2001, vol. 98, No. 11, pp. 6336-6341.
Ikonen, M. et al., "Interaction between the Alzheimer's survival peptide humanin and insulin-like growth factor-binding protein 3 regulates cell survival and apoptosis," *PNAS*, Oct. 28, 2003, vol. 100, No. 22, pp. 13042-13047.
Iribarren, P. et al., "Role of Formlyl Peptide Receptor-Like 1(FPRL 1IFPR2) in Mononuclear Phagocyte Responses in Alzheimer Disease," *Immunologic Research*, 2005, vol. 31, pp. 165-176.
Jiang, J. et al., "Generation of Insulin-Producing Islet-Like Clusters from Human Embryonic Stem Cells," *Stem Cells*, 2007, vol. 25, pp. 1940-1953.
Kayali, A.G. et al., "Limited Capacity of Human Adult Islets Expanded in Vitro to Redifferentiate Into Insulin-Producing 13-Cells," *Diabetes*, Mar. 2007, vol. 56, pp. 703-708.
Kim et al., "Rosiglitazone protects the pancreatic b-cell death induced by cyclosporine", *A. Biochem. Biophys. Res. Commun.*, vol. 390, 2009, pp. 763-768.
King, A.J.F. et al., "Normal Relationship of 13- and Non-j3-Cells Not Needed for Successful IsletTransplantation," *Diabetes*, Sep. 2007, vol. 56, pp. 2312-2318.
Lee, K-W. et al., "The IGFBP-3 Partner, Humanin, Protects Beta Cells From Apoptosis in Vitro and Improves Glucose Tolerance in the Nod Model in Vivo," *Growth Hormone & IGF Research*, Abstracts, 3'• In!. Congress of GRS & IGF Society, 2006, vol. 16, Suppl B, Oral presentations: Nov. 13, 2006, Abstract No. OR08-4, pp. S15-S16.
Lehmann, R. et al., "Superiority of Small Islets in Human Islet Transplantation," *Diabetes*, Mar. 2007, vol. 56, pp. 594-603.
Luciano et al., "Cytoprotective Peptide Humanin Binds and Inhibits Proapoptotic Bcl-2/Bax Family Protein BimEL", *j. Biol. Chem.*, vol. 280, 2005, pp. 15825-15835.
Nishimoto, I. et al., "Unravelling the role of Humanin," *TRENDS in Molecular Medicine*, Mar. 2004, vol. 10, No. 3, pp. 102-105.
O'Brien, BA et al., "Apoptosis Is the Mode of l3-Cell Death Responsible for the Development of IDDM in the Nonobese Diabetic (NOD) Mouse," *Diabetes*, May 1997, vol. 46, pp. 750-757.
Paraskevas, S. et al., "Activation and expression of ERK, JNK, and p38 MAP-kinases in isolated islets of Langerhans: implications for cultured islet survival," *FEBS Letters*, 1999, vol. 455, pp. 203-208.
Park, P. et al., "The Neuro-Survival Peptide, Humanin, Protects 13 Cells from Apoptosis In Vitro and Improves Glucose Tolerance in the NOD Model In Vivo," *The Endocrine Society Program & Abstracts, 8F1h Annual Meeting*, Jun. 24-27, 2006, Boston, MA, Abstract No. OR26-2, p. 110.
Parkash, J. et al., Tumor Necrosis Factor-a-Induced Changes in Insulin-Producing 13-Cells, *The Anatomical Record Part A*, 2005, vol. 286A, pp. 982-993.

(Continued)

*Primary Examiner* — Elly-Gerald Stoica
(74) *Attorney, Agent, or Firm* — Morgan, Lewis & Bockius LLP; Annette S. Parent

(57) ABSTRACT

The present invention is based on the discovery that Humanin and humanin analogues protect pancreatic beta cells in vitro and in vivo from apoptosis. Accordingly, humanin and its analogues are useful for preventing and treating diabetes and promoting beta cell survival in a number of applications.

2 Claims, 5 Drawing Sheets

(56) References Cited

OTHER PUBLICATIONS

Rajah, R. et al., "Insulin-like Growth Factor (IGF)-binding Protein-3 Induces Apoptosis and Mediates the Effects of Transforming Growth Factor-131 on Programmed Cell Death through a p53- and IGF-independent Mechanism," *The Journal of Biological Chemistry*, May 2, 1997, vol. 272, No. 18, pp. 12181-12188.

Shim, M.L. et al., "Insulin-like growth factor binding protein-3 is a novel mediator of apoptosis in insulin-secreting cells," *Growth Honnone IGF Research*, 2004, vol. 14, pp. 216-225.

Stephens, L.A. et al., Tumor Necrosis Factor-a-Activated Cell Death Pathways in NIT-I Insulinoma Cells and Primary Pancreatic 13 Cells, *Endocrinology*, 1999, vol. 140, No. 7, pp. 3219-3227.

Thomas, D. et al., Proapoptotic Bax is Hyperexpressed in Isolated Human Islets Compared With Antiapoptotic BCL-2, *Transplantation*, Dec. 15, 2002, vol. 74, No. 11, pp. 1489-1490.

Tobiasch, E. et al., "Heme Oxygenase-I Protects Pancreatic [3 Cells From Apoptosis Caused by Various Stimuli," *Journal of Investigation Medicine*, Nov. 2001. vol. 49, No. 6, pp. 566-571.

Wang et al., "Maintenance of beta cell function an dsurvival following islet isolation requires re-establishment of islet-matrix relationship", *J. Endocrino*, vol. 163, 1999, pp. 181-190.

Yatoh, S. et al., "Differentiation of Affinity-Purified Human Pancreatic Duct Cells to [3-Cells," *Diabetes*, Jul. 2007, vol. 56, pp. 1802-1809.

Yechoor et al., "Gene therapy for diabetes mellitus," *Gene Therapy*, vol. 12, 2005, pp. 101-107.

Batzer, M. et al., "Enhanced evolutionary PCR using oligonucleotides with inosine at the 3'-terminus", *Nucleic Acids Research*, vol. 19, No. 18, p. 5081 (1991).

Berendsen, H., "A Glimpse of the Holy Grail?", *Science*, vol. 282, pp. 642-643 (1998).

Bradley, C. and Barrick, D., "Limits of Cooperativity in a Structurally Modular Protein: Response of the Notch Ankyrin Domain to Analogous Alanine Substitutions in Each Repeat", *Journal of Molecular Biology*, vol. 324, pp. 373-386 (2002).

Ngo, J. et al., "Computational Complexity, Protein Structure Prediction, and the Levinthal Paradox", *The Protein Folding Problem and Tertiary Structure Prediction*, K. Mera and S. Le Grand, Eds., pp. 491-494 (1994).

Ohtsuka, E. et al., "An alternative Approach to Deoxyoligonucleotides as Hybridization Probes by Insertion of Deoxyinosine at Ambiguous Codon Positions", *The Journal of Biological Chemistry*, vol. 260, No. 5, pp. 2605-2608 (1985).

Rossolini, G. et al., "Use of deoxyinosine-containing primers vs degenerate primers for polymerase chain reaction based on ambiguous sequence information", *Molecular and Cellular Probes*, vol. 8, pp. 91-98 (1994).

Rudinger, J., "Characteristics of the amino acids as components of a peptide hormone sequence", Peptide Hormones, J.A. Parsons, Ed., pp. 1-7 (1976).

Sigma-Genosys, "Designing Custom Peptides", *Custom Peptide Synthesis*, pp. 1-2 (2004).

The On-line Medical Dictionary, Definition of Analogue, pp. 1-5 (2005).

Vagner, J. et al., "Peptidomimetics, a synthetic tool of drug discovery", *Curr. Opin. Chem. Biol.*, vol. 12, No. 3, pp. 292-296 (2008).

Voet, D. and Voet, J., *Biochemistry, Second Edition*, John Wiley & Sons, Inc., pp. 235-241 (1995).

* cited by examiner

METHOD OF TREATMENT OF TYPE-1 DIABETES WITH HUMANIN ANALOGUES

CROSS-REFERENCES TO RELATED APPLICATIONS

This application is a divisional application of U.S. patent application Ser. No. 12/210,856 filed on Sep. 15, 2008, now U.S. Pat. No. 7,998,928 issued Aug. 16, 2011 and claims priority to U.S. Provisional Application No. 60/972,596 filed on Sep. 14, 2007, all of which are incorporated herein by reference in their entirety.

BACKGROUND OF THE INVENTION

Type I diabetes is an autoimmune disease characterized by the progressive destruction of pancreatic beta cells following infiltration of the islet by lymphocytes. This results in insulin deficiency.

Apoptosis is the primary mode of beta cell death during development of Type-1 diabetes (O'Brien et al. (1997) *Diabetes* 46:750-57). IL-1, TNF-alpha and IFN-gamma are released by T cells and macrophages during this autoimmune response and are important mediators of beta cell destruction (Eizirik and Mandrup-Poulsen (2001) *Diabetologia* 44:2115-2133).

Insulin-like Growth Factor Binding Protein-3 (IGFBP-3) induces apoptosis in a manner unrelated to its IGF binding (Rajah et al. (1997) *J Biol Chem.* 272:12181-88). Pro-inflammatory Th1 cytokines increases intranuclear aggregation of endogenous IGFBP-3 and addition of exogenous IGFBP-3 to beta cells induces apoptosis (Shim et al. (2004) *Growth Horm IGF Res.* 14:216-25). IGFBP-3 is one of a number of peptides that includes insulin, leptin, adiponectin, and resistin, that have been shown to act in the central nervous system to regulate glucose metabolism (Muse et al. (20070 *J Clin Invest.* 117:1670-78; Obici et al. (2002) *Nat Med* 8:1376-82). Beta cell loss by apoptosis also occurs after islet graft (Paraskevas et al. (1999) *FEBS Lett.* 455:203-8); Tobiasch et al. (2001) *J Investig Med.* 49:566-71). Recent studies have demonstrated that isolated human islets express the pro-apoptotic protein Bax at higher level than the anti-apoptotic protein Bcl-2 (Thomas et al. (2002) *Transplantation* 74:1489).

Over a million people in the U.S. have type I diabetes. According to the American Diabetes Association, the disease causes thousands of deaths every year and costs more than $20 billion annually. There is currently no effective therapeutic or preventative agent available for Type I diabetes.

Humanin (HN) is a recently described 24-amino acid peptide. HN was independently cloned as a neuroprotective protein, a BAX antagonist, and as an IGFBP-3 binding partner in a yeast two-hybrid assay (Hashimoto et al. (2001) *Proc. Natl. Acad. Sci. USA* 98:6336-41; Guo et al. (2003) *Nature* 423: 456-61; Ikonen et al. (2003) *Proc. Natl. Acad. Sci USA* 100: 13042-47). HN is transcribed from an open reading frame within the mitochondrial 16S ribosomal RNA in mammals (Hashimoto et al., 2001). HN is both an intracellular and secreted protein. HN has been detected in normal mouse testis and colon (by immunoblot and immunohistochemical analyses), as well as in cerebrospinal fluid (CSF), seminal fluid, and serum. Levels in CSF are few orders of magnitude higher than that in circulation. Similar or identical FIN cDNA sequences have since been identified in plants, nematodes, rats, mice, and many other species, demonstrating that it is highly conserved along evolution (Guo et al., 2003).

BRIEF SUMMARY OF THE INVENTION

The present invention is based on the discovery that humanin and humanin analogues protect pancreatic beta cells in vitro and in vivo from apoptosis. Accordingly, humanin and its analogues are useful for preventing and treating diabetes and promoting beta cell survival in a number of applications.

In some embodiments, the invention is drawn to a method of treating diabetes in an individual in need thereof, comprising administering a composition comprising humanin or a humanin analogue to said individual in an amount effective to improve survival of pancreatic beta cells, thereby treating diabetes. In some embodiments, the diabetes is type 1 diabetes. In some embodiments, the diabetes is type 2 or gestational diabetes. In some embodiments, the composition is administered more than once, e.g., on a regular dosage schedule. Improved survival of pancreatic beta cells is determined relative to a control, the design of which is understood in the art. For example improved survival can be determined relative to survival of pancreatic beta cells in an individual with diabetes, or an averaged value of survival in a population of individuals with diabetes.

In some embodiments, the invention is drawn to a method of preventing diabetes in an individual in need thereof, comprising administering a composition comprising humanin or a humanin analogue to said individual in an amount effective to improve survival of pancreatic beta cells, thereby preventing diabetes. In some embodiments, the individual has pre-diabetes or impaired glucose tolerance. In some embodiments, the individual is at risk of developing diabetes. In some embodiments, the composition is administered more than once, e.g., on a regular dosage schedule.

In some embodiments, the invention is drawn to a method of improving survival of a population of pancreatic beta cells, comprising contacting said population with a composition comprising humanin or a humanin analogue in an amount effective to improve survival of said population, as compared to a control, e.g., an untreated population of pancreatic beta cells. In some embodiments, the population of pancreatic beta cells comprises cells from more than one individual. In some embodiments, the population of pancreatic beta cells comprises cells from a single individual. In some embodiments, the cells are human. In some embodiments, the population of pancreatic beta cells is in an in vitro culture.

In some embodiments, the invention is drawn to improving survival of a pancreatic beta cell transplant, comprising administering a composition comprising humanin or a humanin analogue to an individual with a pancreatic beta cell transplant, in an amount effective to improve survival of said transplant as compared to a control. For example, survival can be compared to the survival of an untreated pancreatic cell transplant. In some embodiments, the composition is administered more than once. In some embodiments, the composition is administered at the same time as the transplant is performed. In some embodiments, the composition is administered after transplantation. In some embodiments, the transplant material is selected from the group consisting of a whole organ transplant (e.g., pancreas), a tissue graft, and a population of cells, e.g., enriched in beta islet cells.

In some embodiments, the humanin analogue is selected from the group consisting of: S14G-HN; C8A-HN; D-Ser14-HN; AGA-HNG; AGA-(D-Ser14)-HN; AGA-(D-Ser14)-HN17; AGA-(C8R)-HNG17; EF-HN; EF-HNA; EF-HNG; EF-AGA-HNG; colivelin; P3R-HN; F6A-HN; F6A-HNG; F6AK21A-HNG; and Z-HN. In some embodiments, the humanin analogue is F6A-HNG (SEQ ID NO:16). In some embodiments, the composition comprises more than one humanin analogue, or humanin in combination with at least one humanin analogue.

In some embodiments, the composition is administered in combination with a second therapeutic, e.g., insulin. In some embodiments, the composition is administered at the same time as the second therapeutic composition. In some embodiments, the composition is administered separate from the second therapeutic composition, e.g., on an independent dosing schedule.

DETAILED DESCRIPTION OF THE INVENTION

A. Introduction

Figure 1:
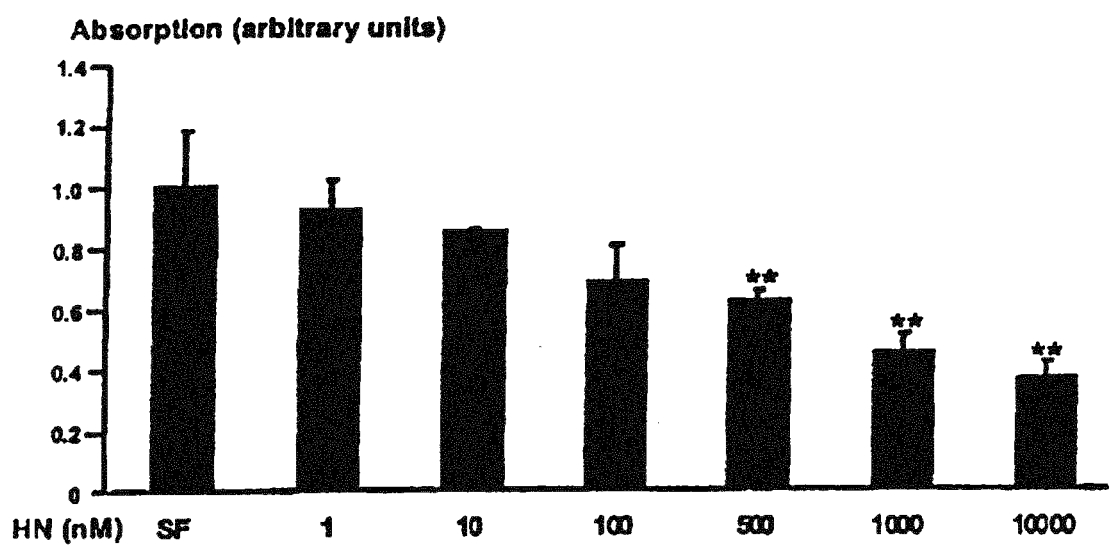
FIG. 1: Humanin is a pancreatic beta cell survival factor. Serum starvation induces apoptosis of NIT-1 cells. Increasing doses of humanin reduced the level of apoptosis. **=p<0.01 vs SF.

The present invention involves a novel therapeutic method for treating and preventing diabetes. Treatment with an effective amount of the small peptide humanin or one of several potent analogues of this peptide has the capacity of: a) preventing the onset of type 1 diabetes in susceptible individuals; b) sustaining the survival and activity of insulin-producing pancreatic beta cells; c) enhancing insulin action and glucose utilization in insulin responsive tissues such as fat. Humanin and humanin analogues act as suppressors of the development of type-1 diabetes in the NOD mouse model and in vitro beta cell cultures, as demonstrated herein. Humanin peptides and analogues have the potential to serve as a single agent or as co-therapy with insulin or other agents in various forms of diabetes or pre-diabetes.

The 24 amino acid humanin peptide was initially proposed to be a neuronal survival factor in the context of Alzheimer's disease. Humanin was later shown to prevent cell death in certain non-neurological models as a Bax antagonist. The cellular receptor, if any, for humanin remains elusive, but may be related to FPRL-1. Humanin activates signaling cascades, including those involving Jak2 and STAT-3 (Matsuoka et al. (2006) CNS Drug Rev. 12:113-22). We found that humanin also binds IGFBP-3. The interaction with IGFBP-3 is especially interesting as IGFBP-3 has been shown to induce insulin resistance both in vivo and in vitro (Kim et al. (2007) Pediatric Res. 61:159-164). Furthermore, it was previously demonstrated that IGFBP-3 induces peripheral insulin resistance independent of IGF-1 binding.

Until we conducted our experiments, however, there was no suggestion that humanin was related to diabetes.

The exact mechanism of humanin's protective activity and interaction with IGFBP-3 may rely on: a) dimerization (Terashita et al. (2003) J Neurochem. 85:1521-38); b) FPRL-1 binding (Guo et al. (2003) Nature 423:456-61); c) tyrosine kinase activation (Jung and Van Nostrand (2003) J Neurochem. 84:266-72), d) STAT-3 activation (Maximov et al. (2002) Med Hypotheses 59:670-73); and e) antagonism of the pro-apoptotic molecules BimEL and Bid (Caricasole et al. (2002) FASEB J. 16:1331-33; Tajima et al. (2002) Neurosci Lett. 324:227-31). In addition, TRIM11 plays a role in the regulation of intracellular humanin levels through ubiquitin-mediated protein degradation pathways.

The invention is based on the discovery that humanin is a potent beta cell survival factor in vitro and in vivo. Humanin is useful for preventing diabetes in genetically at-risk individuals; treating diabetes, particularly type 1 diabetes; promoting islet transplant survival; stabilizing large donor sources of beta cells; and activating endogenous beta cell regeneration with modulation of the autoimmune response (a putative humanin receptor is found on white blood cells and macrophages (Iribarren et al. (2005) Immunol Res., 31:165-76).

B. Definitions

As used herein, "diabetes" refers to the broad class of disorders characterized by impaired insulin production and glucose tolerance. Diabetes includes type 1 and type 2 diabetes (also called juvenile and adult-onset, respectively), gestational diabetes, prediabetes, insulin resistance, metabolic syndrome, and impaired glucose tolerance. Common symptoms include frequent urination, excessive thirst, extreme hunger, unusual weight loss, increased fatigue, irritability, and blurry vision. Diagnosis of these individual disorders is described in more detail below.

Type I diabetes is also known as Insulin Dependent Diabetes Mellitus (IDDM), Type 1 diabetes, and juvenile diabetes. The terms are used interchangeably herein. Treatment and diagnosis of the disease is described in more detail below.

Humanin is a secreted peptide defined by the 24 amino acid sequence of SEQ ID NO:1: MAPRGFSCLLLLT-SEIDLPVKRRA. Humain also includes substantially similar peptides and analogues, as defined herein. Humanin activities include IGFBP-3 binding; inducing cell signaling and STAT-3 activation; reducing apoptosis of neuronal cells; and improving survival of pancreatic beta islet cells.

"Humanin analogues," "humanin derivatives," and equivalent terms, refer to peptides with at least one humanin activity. Humanin analogues are often more potent than humanin itself. One of skill can determine whether any particular peptide is a humanin analogue by determining whether the peptide is capable of neuroprotection in an established humanin assay, e.g., as described in Chiba et al. (2005) J. Neuroscience 25:10252-61.

Generally, the humanin analogue comprises 17-50 amino acids comprising the amino acid sequence of SEQ ID NO:19. As used herein, an amino acid sequence providing the designation (x/y), as in SEQ ID NO:19, indicates that either amino acid x or amino acid y can be used at the indicated position. Analogues include, but are not limited to those shown in Table 1.

TABLE 1

Humanin analogues

| NAME | SEQ ID NO | SEQUENCE |
| --- | --- | --- |
| Humanin | 1 | MAPRGFSCLLLLTSEIDLPVKRRA |
| S14G-HN (HNG) | 2 | MAPRGFSCLLLLTGEIDLPVKRRA |
| C8A-HN (HNA) | 3 | MAPRGFSALLLLTSEIDLPVKRRA |
| D-Ser14-HN | 4 | MAPRGFSCLLLLTS*EIDLPVKRRA |
| AGA-HNG | 5 | MAPAGASCLLLLTGEIDLPVKRRA |
| AGA-(D-Ser14)-HN | 6 | MAPAGASCLLLLTS*EIDLPVKRRA |
| AGA-(D-Ser14)-HN17 | 7 | PAGASCLLLLTS*EIDLP |
| AGA-(C8R)-HNG17 | 8 | PAGASRLLLLTGEIDLP |
| EF-HN | 9 | EFLIVIKSMAPRGFSCLLLLTSEIDLPVKRRA |
| EF-HNA | 10 | EFLIVIKSMAPRGFSALLLLTSEIDLPVKRRA |
| EF-HNG | 11 | EFLIVIKSMAPRGFSCLLLLTGEIDLPVKRRA |
| EF-AGA-HNG | 12 | EFLIVIKSMAPAGASCLLLLTGEIDLPVKRRA |
| Colivelin | 13 | SALLRSPIPA-PAGASRLLLLTGEIDLP |
| P3R-HN | 14 | MARRGFSCLLLSTTATDLPVKRRT |
| F6A-HN | 15 | MAPRGASCLLLLTGEIDLPVKRRA |
| F6A-HNG | 16 | MAPRGASCLLLLTGEIDLPVKRRA |
| F6AK21A-HNG | 17 | MAPRGASCLLLLTGEIDLPVARRA |
| Z-HN | 18 | MAKRGLNCLPHQVSEIDLSVQKRI |
| Consensus sequence | 19 | (P/R/A)(R/A/G)(G/A)(F/A)S(C/R)LLL(L/S)T(S/T/G)(E/A)(I/T)DLP |

S* indicates D-Serine

Some of the humanin analogues have increased potency compared to humanin, or slightly altered activities. Z-HN (SEQ ID NO:18) promotes survival and activates STAT-3 and ERK in NIT cells with a two-fold greater potency than humanin. F6AK21A-HNG (SEQ ID NO: 17) and F6A-HNG (SEQ ID NO:16) demonstrate similar activities with even greater potency. F6A-HNG, however, is devoid of IGFBP-3 binding activity.

"Pancreatic beta cells," "beta islet cells," and similar terms refer a population of pancreatic endocrine cells found in the Islets of Langerhans. Beta islet cells produce and secrete insulin and amylin into the bloodstream.

As used herein, "improving cell survival" refers to an increase in the number of cells that survive a given condition, as compared to a control, e.g., the number of cells that would survive the same conditions in the absence of treatment. Conditions can be in vitro, in vivo, ex vivo, or in situ. Improved cell survival can be expressed as a comparative value, e.g., twice as many cells survive if cell survival is improved two-fold. Improved cell survival can result from a reduction in apoptosis, an increase in the life-span of the cell, or an improvement of cellular function and condition. In some embodiments, cell survival is improved by 5, 10, 20, 30, 40, 50, 60, 70, 80, 90 or 100%, as compared to control levels. In some embodiments, cell survival is by two-, three-, four-, five-, or ten-fold of control levels. Alternatively, improved cell survival can be expressed as a percentage decrease in apoptosis. In some embodiments, for example, apoptosis is reduced by 10, 20, 30, 40, 50, 60, 70, 80, 90 or up to 100%, as compared to a control sample.

The term "preventing a disorder" as used herein, is not intended as an absolute term. Instead, prevention, e.g., of type 1 diabetes, refers to delay of onset, reduced frequency of symptoms, or reduced severity of symptoms associated with the disorder. Prevention therefore refers to a broad range of prophylactic measures that will be understood by those in the art. In some circumstances, the frequency and severity of symptoms is reduced to non-pathological levels, e.g., so that the individual does not need traditional insulin replacement therapy. In some circumstances, the symptoms of an individual receiving the compositions of the invention are only 90, 80, 70, 60, 50, 40, 30, 20, 10, 5 or 1% as frequent or severe as symptoms experienced by an untreated individual with the disorder.

Similarly, the term "treating a disorder" is not intended to be an absolute term. In some aspects, the compositions of the invention seek to reduce the loss of insulin producing cells that lead to diabetic symptoms. In some circumstances, treatment with the leads to an improved prognosis or a reduction in the frequency or severity of symptoms.

"An individual in need of treatment or prevention" refers to an individual that has been diagnosed with type 1 diabetes, type 2 diabetes, gestational diabetes, pre-diabetes, insulin resistance, metabolic syndrome, or impaired glucose tolerance, or one that is at risk of developing any of these disorders. Individuals in need of treatment also include those that have suffered an injury, disease, or surgical procedure affecting the pancreas, or individuals otherwise impaired in their ability to make insulin. Such individuals can be any mammal, e.g., human, dog, cat, horse, pig, sheep, bovine, mouse, rat, rabbit, or primate.

A "transplant," as used herein, refers to the introduction of cells into an individual (recipient or host). A pancreatic beta cell transplant refers to a transplant that includes beta islet cells, but is not necessarily composed entirely of beta islet cells. The transplanted cells can be introduced as an entire organ (e.g., a pancreas), a largely intact tissue sample (e.g., a tissue graft), or as a disaggregated population of cells (e.g., enriched for beta islet cells) (Eisenbarth (2007) *J. Clin. Endocrinol. & Metabol.* 92:2403-07; King et al. (2007) *Diabetes* 56:2312-18). The introduced cells can be from another individual (donor) or from the same individual. In some cases, cells are removed from an individual, cultured under favorable conditions, and replaced. In some cases, undifferentiated or partially differentiated cells can be cultured under appropriate conditions to differentiate into beta islet cells, and transplanted into an individual. See e.g., Yatoh et al. (2007) *Diabetes* 56:1802-09; Jiang et al. (2007) *Stem Cells* 25:1940-53; and Claibom and Stoffers (2008) Mt Sinai J Med 75:362-71.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that otherwise are expressed abnormally, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The terms "nucleic acid" and "polynucleotide" are used interchangeably.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polyp eptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Sequences are "substantially identical" if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, designated region as measured using one of the following sequence comparison algorithms or by manual alignment and visual inspection, or across the entire sequence where not indicated. The invention provides polypeptides or polynucleotides encoding polypeptides that are substantially identical, or comprising sequences substantially identical, to the polypeptides exemplified herein (e.g., humanin). This definition also refers to the complement of a nucleotide test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

C. Expression and Purification of Polypeptides

Naturally-occurring, synthetic, or recombinant polypeptides of the invention can be purified for use in compositions and functional assays. Naturally-occurring polypeptides of the invention can be purified from any source. Recombinant polypeptides can be purified from any suitable expression system (e.g., mammalian, insect, yeast, or bacterial cell culture).

The peptides of the present invention (i.e., humanin and humanin analogues) may include both modified peptides and synthetic peptide analogues. Peptides maybe modified to improve formulation and storage properties, or to protect labile peptide bonds by incorporating non-peptidic structures. Peptides of the present invention may be prepared using methods known in the art. For example, peptides may be produced by chemical synthesis, e.g., using solid phase techniques and/or automated peptide synthesizers. In certain instances, peptides may be synthesized using solid phase strategies on an automated multiple peptide synthesizer (Abimed AMS 422) using 9-fluorenylmethyloxycarbonyl (Fmoc) chemistry. The peptides can then be purified by reversed phase-HPLC and lyophilized.

For recombinant approaches, the present invention includes isolated nucleic acids encoding the polypeptides disclosed herein, expression vectors comprising the nucleic acids, and host cells comprising the expression vectors. More particularly, the invention provides isolated nucleic acids encoding humanin peptides and humanin peptide analogues having humanin activities, the peptides including, but not limited to, the peptides having a sequence selected from the group consisting of SEQ ID NOS:1-19.

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

The polypeptides of the invention may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., *Current Protocols in Molecular Biology* (1995 supplement); and Sambrook et al. MOLECULAR CLONING: A LABORATORY MANUAL, 2nd Ed., (1989)).

A number of procedures can be employed when polypeptides are being purified. For example, polypeptides can be purified using ion exchange or immunoaffinity columns.

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration.

Other methods that rely on solubility of proteins, such as cold ethanol precipitation, are well known to those of skill in the art and can be used to fractionate complex protein mixtures.

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

Immunoaffinity chromatography using antibodies raised to a variety of affinity tags such as hemagglutinin (HA), FLAG, Xpress, Myc, hexahistidine, glutathione S transferase (GST) and the like can be used to purify polypeptides. The His tag will also act as a chelating agent for certain metals (e.g., Ni) and thus the metals can also be used to purify His-containing polypeptides. After purification, the tag is optionally removed by specific proteolytic cleavage.

It will be apparent to one of skill that chromatographic techniques can be performed at any scale and using equipment from many different manufacturers (e.g., Pharmacia Biotech).

D. Cell Culture and In Vitro Applications

In some embodiments, the compositions of the present invention are used to improve the survival of pancreatic beta cells in culture. Cells to be cultured include explants and primary and/or transformed cell cultures derived from patient tissues. Such methods are useful for maintaining and/or improving the viability of a donor source for transplant. In some cases, the population of pancreatic beta cells is expanded in culture.

Methods of cell culture are well known in the art. See, e.g., Freshney et al., Culture of Animal Cells, A Manual of Basic Technique (3rd ed. 1994), and the references cited therein for a discussion of cell culture conditions and how to isolate and culture cells from patients. Conditions for pancreatic cells in particular have been described (Lehmann et al. (2007) *Diabetes* 56:594-603 and King et al. (2007) *Diabetes* 56:2312-18).

In some embodiments, the cultured cells are initially undifferentiated or partially differentiated. Conditions for differentiating cells into pancreatic beta cells are described in Yatoh et al. (2007) *Diabetes* 56:1802-09 and Jiang et al. (2007) *Stem Cells* 25:1940-53.

This aspect of the present invention relies upon routine techniques in the field of cell culture. In general, the cell culture environment includes consideration of such factors as the substrate for cell growth, cell density and cell contract, the gas phase, the medium, and temperature.

Incubation of cells is generally performed under conditions known to be optimal for cell survival. Such conditions may include, for example, a temperature of approximately 37° C. and a humidified atmosphere containing approximately 5% $CO_2$. The duration of the incubation can vary widely, depending on the desired results. Proliferation is conveniently determined using $^3H$ thymidine incorporation or BrdU labeling.

Plastic dishes, flasks, or roller bottles may be used to culture cells according to the methods of the present invention. Suitable culture vessels include, for example, multi-well plates, Petri dishes, tissue culture tubes, flasks, roller bottles, and the like.

Cells are grown at optimal densities that are determined empirically based on the cell type. Cultured cells are normally grown in an incubator that provides a suitable temperature, e.g., the body temperature of the animal from which is the cells were obtained, accounting for regional variations in temperature. Generally, 37° C. is the preferred temperature for cell culture. Most incubators are humidified to approximately atmospheric conditions.

Defined cell media are available as packaged, premixed powders or presterilized solutions. Examples of commonly used media include MEM-α, DME, RPMI 1640, DMEM, Iscove's complete media, or McCoy's Medium (see, e.g., GibcoBRL/Life Technologies Catalogue and Reference Guide; Sigma Catalogue). Typically, MEM-α or DMEM are used in the methods of the invention. Defined cell culture media are often supplemented with 5-20% serum, typically heat inactivated serum. The culture medium is usually buffered to maintain the cells at a pH preferably from about 7.2 to about 7.4. Other supplements to the media typically include, e.g., antibiotics, amino acids, and sugars, and growth factors.

E. Pharmaceutical Compositions

The peptides of the present invention can be administered with a suitable pharmaceutical excipient as necessary. One of skill will understand that the composition will vary depending on mode of administration and dosage unit.

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, about 0.1% to about 75%, about 0.1% to 50%, or about 0.1% to 10% by weight of a conjugate of the present invention or a combination thereof, with the remainder consisting of suitable pharmaceutical carrier and/or excipients. Appropriate excipients can be tailored to the particular composition and route of administration by methods well known in the art. See, e.g., *Remington's Pharmaceutical Sciences*, 18TH ED., Mack Publishing Co., Easton, Pa. (1990).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The compositions can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; coloring agents; and flavoring agents. The compositions may also comprise biodegradable polymer beads, dextran, and cyclodextrin inclusion complexes.

For oral administration, the compositions can be in the form of tablets, lozenges, capsules, emulsions, suspensions, solutions, syrups, sprays, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the conjugate or combination of conjugates, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The conjugates can also be formulated into a suppository disposed, for example, in a polyethylene glycol (PEG) carrier.

Liquid compositions can be prepared by dissolving or dispersing a conjugate or a combination of conjugates and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The conjugates of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

One of ordinary skill in the art understands that the dose administered will vary depending on a number of factors, including, but not limited to, the particular peptide composition to be administered, the mode of administration, the type of application (e.g., prophylactic, therapeutic, etc.), the age of the patient, and the physical condition of the patient. Preferably, the smallest dose and concentration required to produce the desired result should be used. Dosage can be appropriately adjusted for children, the elderly, debilitated patients, and patients with cardiac and/or liver disease. Further guidance can be obtained from studies known in the art using experimental animal models for evaluating dosage. The humanin or humanin analog can be formulated without undue experimentation for administration to a mammal, including humans, as appropriate for the particular application. Additionally, proper dosages of the compositions can be determined without undue experimentation using standard dose-response protocols.

F. Methods of Administration

Administration of the peptides of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra joint, parenteral, intra-arteriole, intradermal, intraventricular, intracranial, intraperitoneal, intralesional, intranasal, rectal, vaginal, or by inhalation. Administration can be targeted directly to pancreatic tissue, e.g., via injection.

The compositions of the invention may be administered repeatedly, e.g., at least 2, 3, 4, 5, 6, 7, 8, or more times, or the composition may be administered by continuous infusion. Suitable sites of administration include, but are not limited to, dermal, mucosal, bronchial, gastrointestinal, anal, vaginal, eye, and ear. The formulations may take the form of solid, semi-solid, lyophilized powder, or liquid dosage forms, such as, for example, tablets, pills, lozenges, capsules, powders, solutions, suspensions, emulsions, suppositories, retention enemas, creams, ointments, lotions, gels, aerosols, or the like, preferably in unit dosage forms suitable for simple administration of precise dosages.

The term "unit dosage form" refers to physically discrete units suitable as unitary dosages for human subjects, each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a conjugate or a combination of conjugates.

Methods for preparing such dosage forms are known to those skilled in the art (see, for example, *Remington's Pharmaceutical Sciences*, 18TH ED., Mack Publishing Co., Easton, Pa. (1990). The composition to be administered contains a quantity of the peptides of the invention in a pharmaceutically effective amount for improving beta islet cell survival. In addition, pharmaceutically acceptable salts of the peptides of the present invention (e.g., acid addition salts) may be prepared and included in the compositions using standard procedures known to those skilled in the art of synthetic organic chemistry and described, e.g., by March, Advanced Organic Chemistry: Reactions, Mechanisms and Structure, 4th Ed., New York, Wiley-Interscience (1992).

In another approach, nucleic acids encoding the polypeptides of the invention are used for transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acids, under the control of a promoter, then express a polypeptide of the present invention, thereby mitigating the effects of a disease associated with reduced insulin production.

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science*, 256:808-813 (1992); Nabel et al., *TIBTECH*, 11:211-217 (1993); Mitani et al., *TIBTECH*, 11:162-166 (1993); Mulligan, *Science*, 926-932 (1993); Dillon, *TIBTECH*, 11:167-175 (1993); Miller, *Nature*, 357:455-460 (1992); Van Brunt, *Biotechnology*, 6(10):1149-1154 (1998); Vigne, *Restorative Neurology and Neuroscience*, 8:35-36 (1995); Kremer et al.,

*British Medical Bulletin*, 51(1):31-44 (1995); Haddada et al., in *Current Topics in Microbiology and Immunology* (Doerfler & Böhm eds., 1995); and Yu et al., *Gene Therapy*, 1:13-26 (1994)).

For delivery of nucleic acids, viral vectors may be used. Suitable vectors include, for example, herpes simplex virus vectors as described in Lilley et al., *Curr. Gene Ther.*, 1(4): 339-58 (2001), alphavirus DNA and particle replicons as decribed in e.g., Polo et al., *Dev. Biol.* (Basel), 104:181-5 (2000), Epstein-Barr virus (EBV)-based plasmid vectors as described in, e.g., Mazda, *Curr. Gene Ther.*, 2(3):379-92 (2002), EBV replicon vector systems as described in e.g., Otomo et al., *J. Gene Med.*, 3(4):345-52 (2001), adeno-virus associated viruses from rhesus monkeys as described in e.g., Gao et al., *PNAS USA.*, 99(18):11854 (2002), adenoviral and adeno-associated viral vectors as described in e.g., Nicklin et al., *Curr. Gene Ther.*, 2(3):273-93 (2002). Other suitable adeno-associated virus (AAV) vector systems can be readily constructed using techniques well known in the art (see, e.g., U.S. Pat. Nos. 5,173,414 and 5,139,941; PCT Publication Nos. WO 92/01070 and WO 93/03769; Lebkowski et al., *Mol. Cell. Biol.*, 8:3988-3996 (1988); Vincent et al. (1990) *Vaccines* 90 (Cold Spring Harbor Laboratory Press); Carter, *Current Opinion in Biotechnology* 3:533-539 (1992); Muzyczka, *Current Topics in Microbiol. and Immunol.*, 158:97-129 (1992); Kotin, *Human Gene Therapy*, 5:793-801 (1994); Shelling et al., *Gene Therapy*, 1:165-169 (1994); and Zhou et al., *J. Exp. Med.*, 179:1867-1875 (1994)). Additional suitable vectors include E1B gene-attenuated replicating adenoviruses described in, e.g., Kim et al., *Cancer Gene Ther.*, 9(9): 725-36 (2002) and nonreplicating adenovirus vectors described in e.g., Pascual et al., *J. Immunol.*, 160(9):4465-72 (1998) Exemplary vectors can be constructed as disclosed by Okayama et al., *Mol. Cell. Biol.*, 3:280 (1983).

Molecular conjugate vectors, such as the adenovirus chimeric vectors described in Michael et al., *J. Biol. Chem.*, 268:6866-6869 (1993) and Wagner et al., *Proc. Natl. Acad. Sci. USA*, 89:6099-6103 (1992), can also be used for gene delivery according to the methods of the invention.

In one illustrative embodiment, retroviruses provide a convenient and effective platform for gene delivery systems. A selected nucleotide sequence encoding a polypeptide of the invention is inserted into a vector and packaged in retroviral particles using techniques known in the art. The recombinant virus can then be isolated and delivered to a subject. Suitable vectors include lentiviral vectors as described in e.g., Scherr et al., *Curr. Gene Ther.*, 2(1):45-55 (2002). Additional illustrative retroviral systems have been described (e.g., U.S. Pat. No. 5,219,740; Miller et al., *BioTechniques*, 7:980-990 (1989); Miller, *Human Gene Therapy*, 1:5-14 (1990); Scarpa et al., *Virology*, 180:849-852 (1991); Burns et al., *Proc. Natl. Acad. Sci. USA*, 90:8033-8037 (1993); and Boris-Lawrie et al., *Curr. Opin. Genet. Develop.*, 3:102-109 (1993).

Other known viral-based delivery systems are described in, e.g., Fisher-Hoch et al., *Proc. Natl. Acad. Sci. USA*, 86:317-321 (1989); Flexner et al., *Ann. N.Y. Acad. Sci.*, 569:86-103 (1989); Flexner et al., *Vaccine*, 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques*, 6:616-627 (1988); Rosenfeld et al., *Science*, 252:431-434 (1991); Kolls et al., *Proc. Natl. Acad. Sci. USA*, 91:215-219 (1994); Kass-Eisler et al., *Proc. Natl. Acad. Sci. USA*, 90:11498-11502 (1993); Guzman et al., *Circulation*, 88:2838-2848 (1993); Guzman et al., *Cir. Res.*, 73:1202-1207 (1993); and Lotze et al., *Cancer Gene Ther.*, 9(8):692-9 (2002).

G. Therapeutic and Prophylactic Applications

In certain aspects, the compositions of the invention are used for the treatment or prevention of a disease or disorder in a subject in need thereof. Examples of diseases or disorders suitable for treatment with the humanin or humanin analogue compositions described herein include, but are not limited to, those disorders characterized by reduced blood insulin levels, or reduced number or function of pancreatic beta islet cells. Such disorders include type 1 and type 2 diabetes, gestational diabetes, pre-diabetes, insulin resistance, metabolic syndrome, and impaired glucose tolerance. The compositions of the invention can be used prophylactically, e.g., for individuals with a genetic predisposition for diabetes.

In some aspects, the compositions of the invention are used to improve prognosis for a beta cell transplant recipient. Humanin is capable of improving the survival of transplanted pancreatic beta cells, as compared to untreated beta cell transplants.

Diabetes mellitus is associated with continuous and pathologically elevated blood glucose concentration; it is one of the leading causes of death in the United States and is responsible for about 5% of all mortality. Diabetes is divided into two major sub-classes: Type 1 (also known as Type I, juvenile diabetes, or Insulin-Dependent Diabetes Mellitus (IDDM)) and Type 2 (also known as Type II, adult onset diabetes, or Non-Insulin-Dependent Diabetes Mellitus (NIDDM)).

The concentration of glucose in the human bloodstream must be controlled within a relatively tight range (60-120 milligrams per deciliter of blood) to maintain normal health. If blood glucose drops too low, a condition known as hypoglycemia results, with symptoms such as faintness, weakness, headache, confusion and personality changes. Excessive blood glucose, or hyperglycemia, may cause tissue damage due to the chemical reactions between the excess glucose and proteins in cells, tissues, and organs. This damage is thought to cause the diabetic complications of blindness, kidney failure, impotence, atherosclerosis, and increased vulnerability to infection.

Diabetes is usually diagnosed following the onset of excessive urination or excessive thirst, often accompanied by weight loss. Often, patients with newly-diagnosed type-1 diabetes have developed some degree of diabetic ketoacidosis by the time the diabetes is recognized. Secondary symptoms include vision changes or unexplainable fatigue. Blood glucose level determination is necessary for an accurate diagnosis. Fasting blood glucose level determination is a standard approach used. However, the oral glucose tolerance test (OGTT) is considered to be more sensitive than fasted blood glucose level. Diabetes mellitus is associated with impaired oral glucose tolerance (OGT). The OGTT thus can aid in the diagnosis (Emancipator (1997) *Am J Clin Pathol* 112:665 74; Type 2 Diabetes Mellitus, Decision Resources Inc., March 2000).

A "pre-diabetic individual" refers to an adult with a fasting blood glucose level greater than 110 mg/dl but less than 126 mg/dl or a 2 hour PG reading of greater than 140 mg/dl but less than 200 mg/dl. A "diabetic individual" refers to an adult with a fasting blood glucose level greater than 126 mg/dl or a 2 hour PG reading of greater than 200 mg/dl.

Impaired glucose tolerance is diagnosed in individuals that have fasting blood glucose levels less than those required for a diagnosis of diabetes, but have a plasma glucose response during the OGTT between normal and diabetics. Impaired glucose tolerance is considered a prediabetic condition, and impaired glucose tolerance (as defined by the OGTT) is a strong predictor for the development of Type II diabetes mellitus (Haffner (1997) *Diabet Med* 14 Suppl 3:S12 8).

The prediabetic state associated with glucose intolerance can also be associated with a predisposition to abdominal obesity, insulin resistance, hyperlipidemia, and high blood pressure (Groop et al. (1997) *Am J Hypertens* 10(9 Pt 2):172S 180S; Haffner (1997) *J Diabetes Complications* 11:69 76; Beck-Nielsen et al. (1996) *Diabet Med* 13 (9 Suppl 6):S78 84).

Type II diabetes mellitus is a progressive disease associated with the reduction of pancreatic function and/or other insulin-related processes, aggravated by increased plasma glucose levels. Thus, Type II diabetes mellitus usually has a prolonged prediabetic phase and various pathophysiological mechanisms can lead to pathological hyperglycemia and impaired glucose tolerance, for instance, abnormalities in glucose utilization and effectiveness, insulin action and/or insulin production in the prediabetic state (Goldberg (1998) *Med Clin North Am* 82:805 21).

Gestational diabetes mellitus (GDM) resembles type 2 diabetes in several respects, involving a combination of relatively inadequate insulin secretion and responsiveness. It occurs in about 2%-5% of all pregnancies and may improve or disappear after delivery. Gestational diabetes is treatable but requires careful medical supervision throughout the pregnancy. About 20%-50% of affected women develop type 2 diabetes later in life. While it may be transient, untreated gestational diabetes can damage the health of the fetus or mother. Risks to the baby include macrosomia (high birth weight), congenital cardiac and central nervous system anomalies, and skeletal muscle malformations.

Early intervention in individuals at risk of developing diabetes, focusing on reducing the pathological hyperglycemia or impaired glucose tolerance may prevent or delay the progression towards diabetes and associated complications. See, e.g., U.S. Pat. No. 7,109,174.

Insulin and sulfonylureas (oral hypoglycemia therapeutic agents) are the two major classes of diabetes medicines prescribed today in the United States. Insulin is prescribed for both Type 1 and Type 2 diabetes, while sulfonylureas are usually prescribed for Type 2 diabetics only. Sulfonylureas stimulate natural insulin secretion and reduce insulin resistance; these compounds do not replace the function of insulin in metabolism. Approximately one-third of patients who receive sulfonylurea become resistant to it. Some Type II diabetics do not respond to sulonylurea therapy. Of patients who do respond to initial treatment with sulfonylureas, 5-10% are likely to experience a loss of sulfonylurea effectiveness after about ten years. See, e.g., U.S. Pat. No. 7,115, 284.

In addition, many anti-diabetic agents, for example, sulfonylureas and thiazolidinediones, have an undesired side effect of increasing body weight. Increased body weight in patients with prediabetic conditions or with diagnosed Type II diabetes mellitus results in deleterious effects due to accentuation of the metabolic and endocrine dysregulation, and obesity per se is a pivotal risk factor for the development and progressive worsening of Type II diabetes mellitus. Thus it is desirable to have an anti-diabetic agent which maintains or lowers body weight. See, e.g., U.S. Pat. No. 7,199,174.

One of skill in the art will appreciate that the humanin peptides and analogues of the invention can be co-administered with other therapeutic agents for the treatment of diabetes. Co-administration can be simultaneous, e.g., in a single pharmaceutical composition or separate compositions. The compositions of the invention can also administered separately from the other therapeutic agent(s), e.g., on an independent dosing schedule.

H. Transplantation of Pancreatic Beta Cells

Another approach for treatment of diabetes is transplant of pancreatic tissue into an individual with reduced blood insulin levels. In some cases, an entire pancreas is transplanted, while in others, smaller tissue grafts are used. Enriched populations of pancreatic beta islet cells can also be transplanted. Diabetic individuals often must receive more than one transplant, as the insulin production of transplanted material tends to decrease over time.

Cells for transplant are generally harvested from a donor individual or population of individuals that are distinct from the recipient (or host). Using these methods, immune suppression of the recipient is necessary to prevent immune rejection by the recipient. Given the unwanted side effects of immunosuppression, however, interest is growing in culturing the recipient's own cells for reintroduction.

Cells to be transplanted can be treated with the compositions of the invention before introduction into the host. Once the pancreatic beta cells are transplanted, the compositions of the invention can be administered to the host systemically or directly to the site of transplantation, as described above.

Methods for culturing pancreatic beta cells are described above. For reviews of transplant techniques, see, e.g., Claiborn and Stoffers (2008) *Mt Sinai J Med* 75:362-71; Eisenbarth (2007) *J. Clin. Endocrinol. & Metabol.* 92:2403-07; and references cited therein.

All publications and patent applications cited in this specification are herein incorporated by reference as if each individual publication or patent application were specifically and individually indicated to be incorporated by reference.

Although the invention is described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

I. Examples

1. Dose-Dependent Protection of Beta Cells from Serum Starvation-Induced Apoptosis by Humanin Secondary to the pro-survival effect of humanin observed in neuronal cells, we hypothesized that humanin could be a survival factor for neuroendocrine beta cells. Mouse NIT-1 insulinoma cells were serum starved for 24 hours as control, and compared to cultures co-incubated with increasing doses of humanin ranging from 1 to 10000 nM.

Conditions were as follows: NIT-1 cells were purchased from ATCC and maintained in F-12 Ham's medium (F12-K) supplemented with 10% FBS (fetal bovine serum), 10% L-glutamine, Penicillin (100 U/ml) and Streptomycin (100 µg/ml), in 25 cm$^2$ tissue culture flasks (Greiner, Frickenhausen, Germany). NIT-1 cells were maintained at 37 C in a 5% $CO_2$/95% air mixture and were passaged twice weekly by trypsination (Invitrogen life technologies, Karlsruhe, Germany). For the experiment, NIT-1 cells were seeded in 96-well plates at a density of 0.128×10$^5$ cells per well. After about 24 hours, medium was changed to FCS-free medium.

Apoptosis was quantified by a specific histone-associated DNA ELISA. Humanin potently protected beta cells from serum-starvation induced apoptosis in a dose dependent manner (FIG. 1).

2. Humanin Inhibits Cytokine-Induced Beta Cell Apoptosis

Apoptosis is the main form of pancreatic beta cell death in animal models of type 1 diabetes mellitus. IFN-γ/TNF-α synergism has been shown to play an important role in autoimmune diabetes in vivo as well as beta cell apoptosis in vitro. In this study, we used a caspase 3/7 specific fluorometric assay (ApoONE, Promega) to measure the degree of apoptosis induction by cytokines in NIT-1 cells.

Cells were cultured as described above. For the experiment, NIT-1 cells were seeded in 96-well plates at a density of $0.128 \times 10^5$ cells per well. After about 24 hours, medium was changed to FCS-free medium and the cells were exposed to TNF-α (5 ng/mL) or were kept untreated as controls. As expected, TNF-α induced apoptosis in NIT-1 cells at 48 hours.

Humanin protects beta cells from cytokine-induced apoptosis and serum starvation induced apoptosis in a dose-dependent manner when measured via caspase 3/7 assay in doses that ranged from 10 to 1000 nM. TNF-α increased apoptosis approximately 40% compared to serum-deprived cells. Humanin protected beta cells from TNF-α induced apoptosis in a dose dependent manner.

3. Humanin Activates ERK and STAT3 in Beta Cells

To investigate the mechanism of Humanin-induced beta cell survival, we treated NIT-1 cells with 100 nM HN in serum free media. Cell lysates were harvested and phosphorylated ERK1/2 and STAT3 were assessed by immunoblotting.

Figure 2:
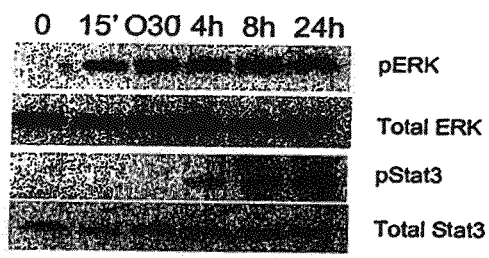
FIG. 2: Humanin activates ERK and STAT3. NIT-1 cells were incubated with 100 nM HN in serum free media as indicated, cell lysates were harvested, and phosphorylated and total ERK1/2 and STAT3 were assessed by immunoblotting.

Phosphorylation of ERK (activation) occurred 15 minutes after adding HN. Phosphorylation of STAT3 (activation) was a later event, 4 hours after addition of HN (FIG. 2).

Figure 3:
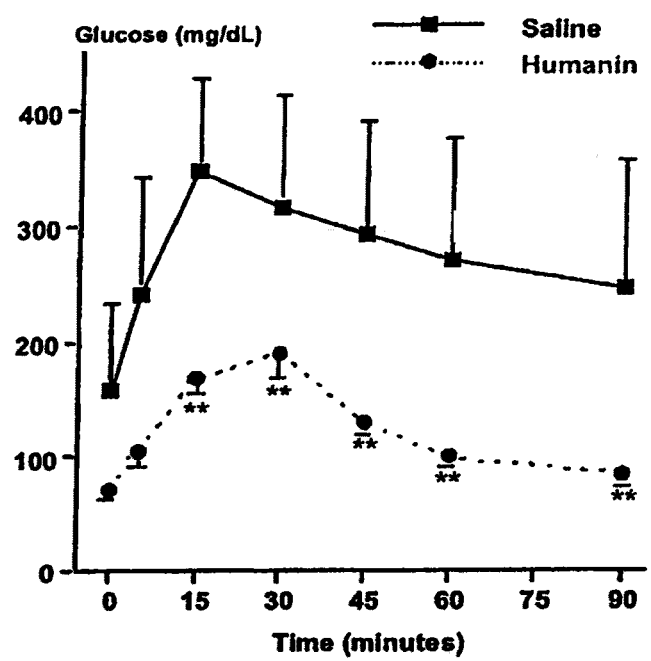
FIG. 3: Humanin improves glucose tolerance in NOD mice. Glucose Tolerance Testing of humanin and saline-treated NOD mice (n=6 mice per group). **=p<0.01 by ANOVA.

4. In Vivo Treatment of NOD Mice with Humanin In Vivo Improves Glucose Tolerance As proof of principle, we examined whether a 6-week course of daily IP injected humanin (0.7 mg/kg/d) to euglycemic 9-week-old NOD mice (Taconic) could improve glucose tolerance as compared to saline-injected control mice (n=12/group). Daily IP injections were tolerated well. There was no difference in food intake or weight in humanin-treated vs. control mice. At the conclusion of the treatment, mice were fasted overnight and divided into groups that were subjected to IP insulin and glucose tolerance testing (n=6/group). Mice that were treated with humanin showed a non-diabetic response to glucose challenge, while control mice showed the expected diabetic profile (FIG. 3). Response to IP insulin tolerance testing was similar in both groups, implying no effect on peripheral insulin sensitivity. We additionally harvested serum, pancreata, and various other organs from these mice for histological studies and analysis of serum humanin, IGFBP-3, and other IGF-related peptides.

5. Humanin Decreases Severity of Insulitis in the NOD Mouse

To test whether administration of humanin regulates the extent of lymphocyte infiltration into pancreatic islets, fixed and embedded pancreatic tissues were examined. Pancreata from humanin-treated NOD mice were formalin fixed, stained with hematoxylin/eosin, and assessed in a blinded fashion to determine the degree of lymphocyte infiltration. Results were compared to tissues from saline-injected control mice. Three or four randomly selected and nonadjacent sections from each pancreas were scored independently by two blind observers and evaluated for mononuclear cell infiltration. Severity of infiltration was classified based on the degree of lymphocytic infiltration as follows: G0—normal (no infiltration); G1—peri-insulitis (mononuclear cells surrounding islets and ducts but no infiltration of the islet architecture); G2—moderate insulitis (mononuclear cells infiltrating less than 50% of the islet architecture); and G3—severe insulitis (more than 50% of the islet tissue infiltrated by lymphocytes, accompanied by a reduction in insulin staining). See Pastorale et al. (2002) *Exp Biol Med (Maywood)* 227:282-89.

Figure 4:
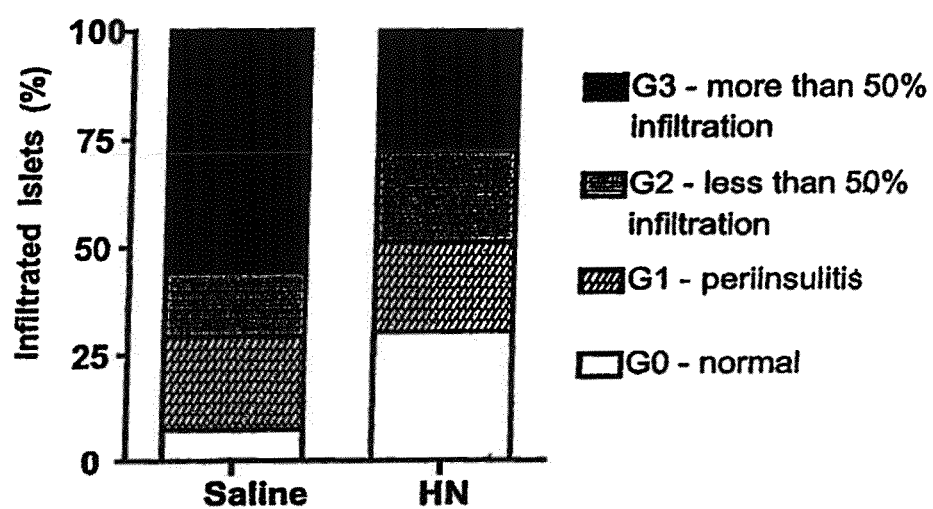
FIG. 4: Humanin treatment decreased insulitis severity. Incidence and severity of insulitis was analyzed busing formalin-fixed and paraffin-embedded pancreatic tissues. Sections were scored as described in the Examples section.

Humanin treatment significantly decreased the total number of islets infiltrated by lymphocytes, as well as the severity of infiltration, as compared to the vehicle-treated negative control mice (FIG. 4). Thus, humanin treatment partially blocks islet inflammation during type 1 diabetes development in NOD mice. Our results indicate that humanin activates endogenous beta cell regeneration and modulates the autoimmune response. As noted above, a putative humanin receptor is found on white blood cells and macrophages.

6. Humanin Delays the Onset of Diabetes in the NOD Mouse

Figure 5:
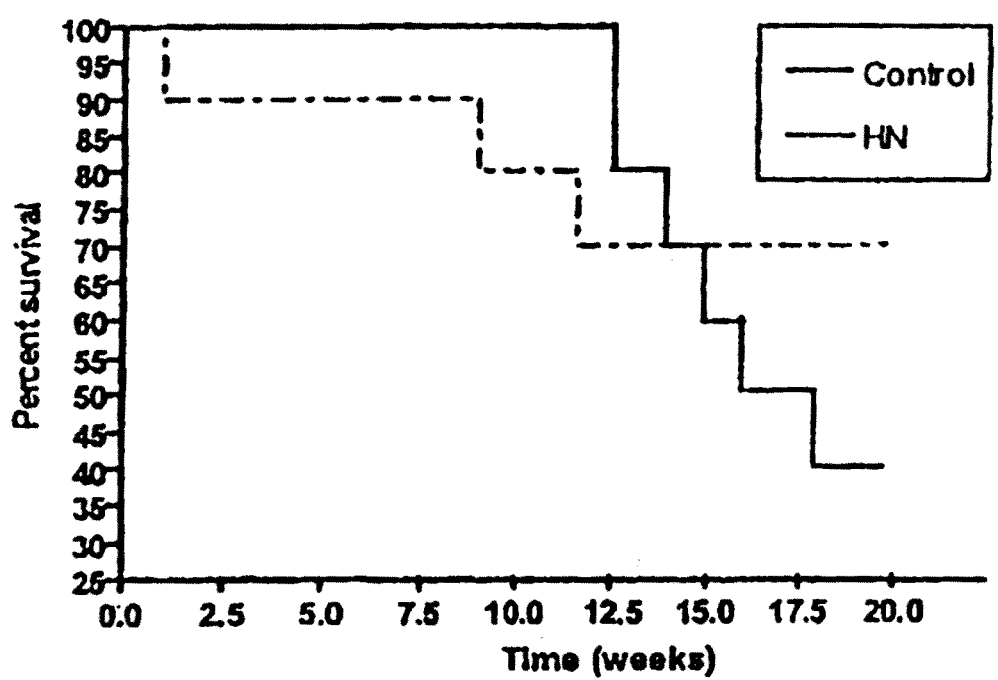
FIG. 5: Humanin delays onset of diabetes in NOD mice. Percent survival is indicative of a disease free state.

Four-week-old female NOD mice were treated with humanin. Before treatment, mice were tested two to three times per week for nonfasting blood glucose levels. Mice with blood glucose levels higher than 300 mg/dL on three consecutive measurements were considered diabetic. Beginning at 5 weeks of age, two groups of NOD mice (n=25 each) were administered (0.7 mg/kg/d) synthetic humanin by IP injection daily (Bachem). NOD mice injected with the same volume of saline served as negative controls. Over a 20-week treatment period, humanin significantly delayed the onset of diabetes (FIG. 5).

7. Humanin Analogue F6A-HNG Treats Type 2 Diabetes in NONcNZO10/LtJ Mice

F6A-HNG does not bind IGFBP-3. Mouse embryonic fibroblasts (MEFs) derived from normal (wild-type) and IGFBP3 deficient mice were used to test the effects of humanin and its analogues on survival. Apoptosis was measured after 24 hours with 100 nM of each peptide by ELISA. F6A-HNG was more potent in normal MEFs; however, HNG and F6A-HNG had equal potency in IGFBP-3 deficient MEFs. The results demonstrate that F6A-HNG is more potent in this assay than humanin analogues that do bind IGFBP-3. The increased potency seems to result from the lack of IGFBP-3 binding, because there is no additional advantage when IGFBP-3 is not present. Thus, F6A-HNG is distinct from previously described humanin derivatives.

NONcNZO10/LtJ mice are a model for obesity-induced type 2 diabetes. NONcNZO10/LtJ mice were injected IP with 25 μg F6A-HNG twice a day for 14 days. Mice were subjected to 6 hour fast followed by an IP GTT on D15. Baseline glucose measurement was taken and the mice were injected IP with 0.5 mg/g glucose. Glucose was sampled at 0 and 90, 120 min.

Mice treated with F6A-HNG displayed significantly better glucose tolerance. The glucose levels at 90 and 120 min were significantly lower in the F6A-HNG treated mice. Thus, F6A-HNG and other humanin analogues are useful in the treatment of type 2 diabetes, as well as the metabolic syndrome associated with obesity.

What is claimed is:

1. A method of treating type I diabetes in an individual in need thereof, said method comprising:
   administering a composition comprising a humanin analogue consisting of SEQ ID NO: 8 to said individual in an amount effective to improve survival of pancreatic beta cells, as compared to an individual with type I diabetes, thereby treating type I diabetes.

2. A method of improving survival of a population of pancreatic beta cells in vitro, said method comprising:
   contacting said population with a composition comprising a humanin analogue consisting of SEQ ID NO: 8 in an amount effective to improve survival of said population, as compared to an untreated population of pancreatic beta cells.

* * * * *

SEQUENCE LISTING

<160> NUMBER OF SEQ ID NOS: 20

<210> SEQ ID NO 1
<211> LENGTH: 24
<212> TYPE: PRT
<213> ORGANISM: Homo sapiens
<220> FEATURE:
<223> OTHER INFORMATION: humanin (HN)

<400> SEQUENCE: 1

Met Ala Pro Arg Gly Phe Ser Cys Leu Leu Leu Leu Thr Ser Glu Ile
 1               5                  10                  15

Asp Leu Pro Val Lys Arg Arg Ala
            20

<210> SEQ ID NO 2
<211> LENGTH: 24
<212> TYPE: PRT
<213> ORGANISM: Artificial Sequence
<220> FEATURE:
<223> OTHER INFORMATION: synthetic humanin (HN) analogue S14G-HN (HNG)

<400> SEQUENCE: 2

Met Ala Pro Arg Gly Phe Ser Cys Leu Leu Leu Leu Thr Gly Glu Ile
 1               5                  10                  15

Asp Leu Pro Val Lys Arg Arg Ala
            20

<210> SEQ ID NO 3
<211> LENGTH: 24
<212> TYPE: PRT
<213> ORGANISM: Artificial Sequence
<220> FEATURE:
<223> OTHER INFORMATION: synthetic humanin (HN) analogue C8A-HN (HNA)

<400> SEQUENCE: 3

Met Ala Pro Arg Gly Phe Ser Ala Leu Leu Leu Leu Thr Ser Glu Ile
 1               5                  10                  15

Asp Leu Pro Val Lys Arg Arg Ala
            20

<210> SEQ ID NO 4
<211> LENGTH: 24
<212> TYPE: PRT
<213> ORGANISM: Artificial Sequence
<220> FEATURE:
<223> OTHER INFORMATION: synthetic humanin (HN) analogue D-Ser14-HN
<221> NAME/KEY: MOD_RES
<222> LOCATION: (14)...(14)
<223> OTHER INFORMATION: Xaa = D-Ser

<400> SEQUENCE: 4

Met Ala Pro Arg Gly Phe Ser Cys Leu Leu Leu Leu Thr Xaa Glu Ile
 1               5                  10                  15

Asp Leu Pro Val Lys Arg Arg Ala
            20

<210> SEQ ID NO 5
<211> LENGTH: 24
<212> TYPE: PRT
<213> ORGANISM: Artificial Sequence
<220> FEATURE:
<223> OTHER INFORMATION: synthetic humanin (HN) analogue AGA-HNG

<400> SEQUENCE: 5

```
Met Ala Pro Ala Gly Ala Ser Cys Leu Leu Leu Leu Thr Gly Glu Ile
 1               5                  10                  15

Asp Leu Pro Val Lys Arg Arg Ala
             20
```

<210> SEQ ID NO 6
<211> LENGTH: 24
<212> TYPE: PRT
<213> ORGANISM: Artificial Sequence
<220> FEATURE:
<223> OTHER INFORMATION: synthetic humanin (HN) analogue AGA-(D-Ser14)-
      HN
<221> NAME/KEY: MOD_RES
<222> LOCATION: (14)...(14)
<223> OTHER INFORMATION: Xaa = D-Ser

<400> SEQUENCE: 6

```
Met Ala Pro Ala Gly Ala Ser Cys Leu Leu Leu Leu Thr Xaa Glu Ile
 1               5                  10                  15

Asp Leu Pro Val Lys Arg Arg Ala
             20
```

<210> SEQ ID NO 7
<211> LENGTH: 17
<212> TYPE: PRT
<213> ORGANISM: Artificial Sequence
<220> FEATURE:
<223> OTHER INFORMATION: synthetic humanin (HN) analogue AGA-(D-Ser14)-
      HN17
<221> NAME/KEY: MOD_RES
<222> LOCATION: (12)...(12)
<223> OTHER INFORMATION: Xaa = D-Ser

<400> SEQUENCE: 7

```
Pro Ala Gly Ala Ser Cys Leu Leu Leu Leu Thr Xaa Glu Ile Asp Leu
 1               5                  10                  15

Pro
```

<210> SEQ ID NO 8
<211> LENGTH: 17
<212> TYPE: PRT
<213> ORGANISM: Artificial Sequence
<220> FEATURE:
<223> OTHER INFORMATION: synthetic humanin (HN) analogue AGA-(C8R)-HNG17

<400> SEQUENCE: 8

```
Pro Ala Gly Ala Ser Arg Leu Leu Leu Leu Thr Gly Glu Ile Asp Leu
 1               5                  10                  15

Pro
```

<210> SEQ ID NO 9
<211> LENGTH: 32
<212> TYPE: PRT
<213> ORGANISM: Artificial Sequence
<220> FEATURE:
<223> OTHER INFORMATION: synthetic humanin (HN) analogue EF-HN

<400> SEQUENCE: 9

```
Glu Phe Leu Ile Val Ile Lys Ser Met Ala Pro Arg Gly Phe Ser Cys
 1               5                  10                  15

Leu Leu Leu Leu Thr Ser Glu Ile Asp Leu Pro Val Lys Arg Arg Ala
             20                  25                  30
```

<210> SEQ ID NO 10
<211> LENGTH: 32

```
<212> TYPE: PRT
<213> ORGANISM: Artificial Sequence
<220> FEATURE:
<223> OTHER INFORMATION: synthetic humanin (HN) analogue EF-HNA

<400> SEQUENCE: 10

Glu Phe Leu Ile Val Ile Lys Ser Met Ala Pro Arg Gly Phe Ser Ala
 1               5                  10                  15

Leu Leu Leu Leu Thr Ser Glu Ile Asp Leu Pro Val Lys Arg Arg Ala
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: synthetic humanin (HN) analogue EF-HNG

<400> SEQUENCE: 11

Glu Phe Leu Ile Val Ile Lys Ser Met Ala Pro Arg Gly Phe Ser Cys
 1               5                  10                  15

Leu Leu Leu Leu Thr Gly Glu Ile Asp Leu Pro Val Lys Arg Arg Ala
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: synthetic humanin (HN) analogue EF-AGA-HNG

<400> SEQUENCE: 12

Glu Phe Leu Ile Val Ile Lys Ser Met Ala Pro Ala Gly Ala Ser Cys
 1               5                  10                  15

Leu Leu Leu Leu Thr Gly Glu Ile Asp Leu Pro Val Lys Arg Arg Ala
            20                  25                  30

<210> SEQ ID NO 13
<211> LENGTH: 27
<212> TYPE: PRT
<213> ORGANISM: Artificial Sequence
<220> FEATURE:
<223> OTHER INFORMATION: synthetic humanin (HN) analogue Colivelin

<400> SEQUENCE: 13

Ser Ala Leu Leu Arg Ser Pro Ile Pro Ala Pro Ala Gly Ala Ser Arg
 1               5                  10                  15

Leu Leu Leu Leu Thr Gly Glu Ile Asp Leu Pro
            20                  25

<210> SEQ ID NO 14
<211> LENGTH: 24
<212> TYPE: PRT
<213> ORGANISM: Artificial Sequence
<220> FEATURE:
<223> OTHER INFORMATION: synthetic humanin (HN) analogue P3R-HN

<400> SEQUENCE: 14

Met Ala Arg Arg Gly Phe Ser Cys Leu Leu Leu Ser Thr Thr Ala Thr
 1               5                  10                  15

Asp Leu Pro Val Lys Arg Arg Thr
            20

<210> SEQ ID NO 15
<211> LENGTH: 24
```

```
<212> TYPE: PRT
<213> ORGANISM: Artificial Sequence
<220> FEATURE:
<223> OTHER INFORMATION: synthetic humanin (HN) analogue F6A-HN

<400> SEQUENCE: 15

Met Ala Pro Arg Gly Ala Ser Cys Leu Leu Leu Leu Thr Ser Glu Ile
 1               5                   10                  15

Asp Leu Pro Val Lys Arg Arg Ala
            20

<210> SEQ ID NO 16
<211> LENGTH: 24
<212> TYPE: PRT
<213> ORGANISM: Artificial Sequence
<220> FEATURE:
<223> OTHER INFORMATION: synthetic humanin (HN) analogue F6A-HNG

<400> SEQUENCE: 16

Met Ala Pro Arg Gly Ala Ser Cys Leu Leu Leu Leu Thr Gly Glu Ile
 1               5                   10                  15

Asp Leu Pro Val Lys Arg Arg Ala
            20

<210> SEQ ID NO 17
<211> LENGTH: 24
<212> TYPE: PRT
<213> ORGANISM: Artificial Sequence
<220> FEATURE:
<223> OTHER INFORMATION: synthetic humanin (HN) analogue F6AK21A-HNG

<400> SEQUENCE: 17

Met Ala Pro Arg Gly Ala Ser Cys Leu Leu Leu Leu Thr Gly Glu Ile
 1               5                   10                  15

Asp Leu Pro Val Ala Arg Arg Ala
            20

<210> SEQ ID NO 18
<211> LENGTH: 24
<212> TYPE: PRT
<213> ORGANISM: Artificial Sequence
<220> FEATURE:
<223> OTHER INFORMATION: synthetic humanin (HN) analogue Z-HN

<400> SEQUENCE: 18

Met Ala Lys Arg Gly Leu Asn Cys Leu Pro His Gln Val Ser Glu Ile
 1               5                   10                  15

Asp Leu Ser Val Gln Lys Arg Ile
            20

<210> SEQ ID NO 19
<211> LENGTH: 17
<212> TYPE: PRT
<213> ORGANISM: Artificial Sequence
<220> FEATURE:
<223> OTHER INFORMATION: synthetic humanin (HN) analogue consensus
      sequence
<221> NAME/KEY: MOD_RES
<222> LOCATION: (1)...(1)
<223> OTHER INFORMATION: Xaa = Pro, Arg or Ala
<221> NAME/KEY: MOD_RES
<222> LOCATION: (2)...(2)
<223> OTHER INFORMATION: Xaa = Arg, Ala or Gly
<221> NAME/KEY: MOD_RES
<222> LOCATION: (3)...(3)
<223> OTHER INFORMATION: Xaa = Gly or Ala
<221> NAME/KEY: MOD_RES
<222> LOCATION: (4)...(4)
```

```
<223> OTHER INFORMATION: Xaa = Phe or Ala
<221> NAME/KEY: MOD_RES
<222> LOCATION: (6)...(6)
<223> OTHER INFORMATION: Xaa = Cys or Arg
<221> NAME/KEY: MOD_RES
<222> LOCATION: (10)...(10)
<223> OTHER INFORMATION: Xaa = Leu or Ser
<221> NAME/KEY: MOD_RES
<222> LOCATION: (12)...(12)
<223> OTHER INFORMATION: Xaa = Ser, Thr or Gly
<221> NAME/KEY: MOD_RES
<222> LOCATION: (13)...(13)
<223> OTHER INFORMATION: Xaa = Glu or Ala
<221> NAME/KEY: MOD_RES
<222> LOCATION: (14)...(14)
<223> OTHER INFORMATION: Xaa = Ile or Thr

<400> SEQUENCE: 19

Xaa Xaa Xaa Xaa Ser Xaa Leu Leu Leu Xaa Thr Xaa Xaa Xaa Asp Leu
 1               5                   10                  15

Pro

<210> SEQ ID NO 20
<211> LENGTH: 6
<212> TYPE: PRT
<213> ORGANISM: Artificial Sequence
<220> FEATURE:
<223> OTHER INFORMATION: synthetic hexahistidine affinity tag, His tag

<400> SEQUENCE: 20

His His His His His His
 1               5
```